US011684333B2

(12) United States Patent
Liao et al.

(10) Patent No.: US 11,684,333 B2
(45) Date of Patent: **\*Jun. 27, 2023**

(54) MEDICAL IMAGE ANALYZING SYSTEM AND METHOD THEREOF

(71) Applicant: National Taiwan University, Taipei (TW)

(72) Inventors: Wei-Chih Liao, Taipei (TW); Wei-Chung Wang, Taipei (TW); Kao-Lang Liu, Taipei (TW); Po-Ting Chen, Taipei (TW); Da-Wei Chang, Taipei (TW)

(73) Assignee: National Taiwan University, Taipei (TW)

( * ) Notice: Subject to any disclaimer, the term of this patent is extended or adjusted under 35 U.S.C. 154(b) by 248 days.

This patent is subject to a terminal disclaimer.

(21) Appl. No.: 17/137,647

(22) Filed: Dec. 30, 2020

(65) Prior Publication Data

US 2021/0204898 A1 Jul. 8, 2021

Related U.S. Application Data

(60) Provisional application No. 62/956,687, filed on Jan. 3, 2020.

(30) Foreign Application Priority Data

Dec. 9, 2020 (TW) .................... 109143455

(51) Int. Cl.
*A61B 6/00* (2006.01)
*G06T 7/11* (2017.01)
(Continued)

(52) U.S. Cl.
CPC .......... *A61B 6/5217* (2013.01); *G06T 7/0012* (2013.01); *G06T 7/11* (2017.01);
(Continued)

(58) Field of Classification Search
CPC ....... A61B 6/5217; A61B 5/055; A61B 6/032; A61B 5/0013; A61B 5/4887;
(Continued)

(56) References Cited

U.S. PATENT DOCUMENTS 10,346,728 B2 * 7/2019 Fu .................... G06V 30/194
10,489,908 B2 * 11/2019 Kiraly ................ G06T 7/0012
(Continued)

FOREIGN PATENT DOCUMENTS

| CN | 109003260 | 12/2018 |
| TW | 201839634 | 11/2018 |
| TW | 201935403 | 9/2019 |

OTHER PUBLICATIONS

Hang Zhou,Targeted attack and security enhancement on texture synthesis based steganography, Journal of Visual Communication and Image Representation,vol. 54, (Year: 2018).*

(Continued)

*Primary Examiner* — Boniface Ngathi N
*Assistant Examiner* — Zainab Mohammed Aldarraji
(74) *Attorney, Agent, or Firm* — Amin, Turocy & Watson, LLP

(57) ABSTRACT

Provided is a medical image analyzing system and a method thereof, which includes: acquiring a processed image having a segmentation label corresponding to a cancerous part of an organ (if present), generating a plurality of image patches therefrom, performing feature analysis on the image patches and model training to obtain prediction values, drawing a receiver operating characteristic curve using the prediction values, and determining a threshold with which determines (Continued)

whether the image patches are cancerous, so as to effectively improve the detection rate of, for example, pancreatic cancer.

26 Claims, 11 Drawing Sheets

(51) Int. Cl.
*G06T 7/00* (2017.01)
*G16H 30/40* (2018.01)
*G16H 50/20* (2018.01)
*A61B 6/03* (2006.01)
*A61B 5/055* (2006.01)

(52) U.S. Cl.
CPC ............ *G16H 30/40* (2018.01); *G16H 50/20* (2018.01); *A61B 5/055* (2013.01); *A61B 6/032* (2013.01); *G06T 2207/10081* (2013.01); *G06T 2207/10088* (2013.01); *G06T 2207/20081* (2013.01); *G06T 2207/20132* (2013.01); *G06T 2207/30096* (2013.01)

(58) Field of Classification Search
CPC . A61B 5/7267; A61B 5/7275; A61B 2576/00; G06T 7/0012; G06T 7/11; G06T 2207/10081; G06T 2207/10088; G06T 2207/20081; G06T 2207/20132; G06T 2207/30096; G06T 2207/20072; G06T 2207/20076; G06T 7/41; G06T 7/45; G16H 30/40; G16H 50/20
See application file for complete search history.

(56) References Cited

U.S. PATENT DOCUMENTS

| | | | |
|---|---|---|---|
| 11,195,062 B2* | 12/2021 | Jaber | ................ G06T 7/10 |
| 2012/0165217 A1 | 6/2012 | Gold et al. | |
| 2017/0076448 A1* | 3/2017 | Chen | ................ G06V 10/46 |
| 2017/0345154 A1* | 11/2017 | Chen | ................ G06T 7/11 |
| 2019/0304092 A1* | 10/2019 | Akselrod-Ballin | ................ G06V 10/454 |
| 2020/0160097 A1* | 5/2020 | Jaber | ................ G06V 20/698 |
| 2022/0319704 A1* | 10/2022 | Feng | ................ G06T 7/0012 |
| 2022/0328189 A1* | 10/2022 | Zhou | ................ G06V 10/7753 |

OTHER PUBLICATIONS

Gabriel Tozatto Zago, Diabetic Retinopathy Detection Based On Deep Learning, 2019 (Year: 2019).*
Sun L, Zhang S, Chen H, Luo L. Brain Tumor Segmentation and Survival Prediction Using Multimodal MRI Scans With Deep Learning. Front Neurosci. Aug. 16, 20196;13:810. doi: 10.3389/fnins.2019.00810. PMID: 31474816; PMCID: PMC6707136. (Year: 2019).*
Taiwanese Office Action for Taiwanese Patent Application No. 109143455 dated Oct. 28, 2021.
Liao, et al. "Radiomic Features Distinguish Pancreatic Cancer from Non-Cancerous Pancreas", DDW archives, May 1, 2020.

* cited by examiner

MEDICAL IMAGE ANALYZING SYSTEM AND METHOD THEREOF

CROSS-REFERENCE TO RELATED APPLICATION

The present application claims the benefit of U.S. Provisional Patent Application No. 62/956,687, filed on Jan. 3, 2020, and the priority from Taiwan Application No. 109143455, filed on Dec. 9, 2020, which are incorporated by reference herein in its entirety.

TECHNICAL FIELD

The present disclosure relates to an image analyzing system and a method thereof, particularly to a medical image analyzing system and a method thereof.

BACKGROUND

In current medical standards, pancreatic cancer is one of the cancers that are difficult to detect early, in which the survival rate drops significantly once tumor size exceeds 2 cm. In the existing technology, computed tomography (CT) imaging is currently the main method for detecting and evaluating pancreatic cancer. However, the detection efficiency of CT imaging still depends on the expertise/experience of the radiologist. For example, approximately 40% of the tumors smaller than 2 cm have been shown to evade detection by radiologist interpretation. This reflects that human image reading and interpretation of CT imaging is interpreter-dependent and prone to errors.

Therefore, it has become an urgent issue in the art on how to provide a medical image analyzing system and a method thereof with improved detection rate applicable to, for example, identifying pancreatic cancer.

SUMMARY

The present disclosure is to provide a medical image analyzing system, comprising: an image preprocessing module configured to process at least one image corresponding to an organ to generate at least one processed image, wherein the processed image comprises a segmentation label corresponding to a cancerous part of the organ (if present); a patch cropping module configured to acquire a plurality of image patches from the processed image; a feature analysis module configured to perform feature analysis on the plurality of image patches to obtain a plurality of feature values corresponding to each of the plurality of image patches; a training module configured to train a full model using the plurality of feature values of each of the plurality of image patches to obtain a plurality of first prediction values corresponding to the respective plurality of image patches; and a threshold selection module configured to plot a first curve based on the plurality of first prediction values and determine a first threshold that is used for determining whether each of the plurality of image patches is cancerous according to the first curve.

The present disclosure is also to provide a medical image analyzing method, comprising: processing at least one image corresponding to an organ to generate at least one processed image, wherein the processed image comprises a segmentation label corresponding to a cancerous part of the organ (if present); acquiring a plurality of image patches from the processed image; performing feature analysis on the plurality of image patches to obtain a plurality of feature values corresponding to each of the plurality of image patches; training a full model using the plurality of feature values of each of the plurality of image patches to obtain a plurality of first prediction values corresponding to the respective plurality of image patches; and plotting a first curve based on the plurality of first prediction values and determining a first threshold that is used for determining whether each of the plurality of image patches is cancerous according to the first curve.

In the aforementioned medical image analyzing system and method thereof, the patch cropping module acquires the plurality of image patches with a square window that moves along an x axis and a y axis of the processed image.

In the aforementioned medical image analyzing system and method thereof, the patch cropping module masks the segmentation label of the processed image and masks the processed image except for the organ, and then acquires the unmasked area of the processed image with the square window moving at a stride of 5 pixels to generate the plurality of image patches.

In the aforementioned medical image analyzing system and method thereof, the patch cropping module masks the processed image except for the segmentation label, and then acquires the unmasked area of the processed image with the square window moving at a stride of 1 pixel to generate the plurality of image patches.

In the aforementioned medical image analyzing system and method thereof, the feature analysis module performs feature analysis using radiomics.

In the aforementioned medical image analyzing system and method thereof, the features employed by the radiomics include: First Order features, Gray Level Co-occurrence Matrix (GLCM) features, Gray Level Dependence Matrix (GLDM) features, Gray Level Run Length Matrix (GLRLM) features, Gray Level Size Zone Matrix (GLSZM) features or Neighboring Gray Tone Difference Matrix (NGTDM) features.

In the aforementioned medical image analyzing system and method thereof, the training module trains the full model using an extreme gradient boosting (XGboost) machine learning algorithm.

The aforementioned medical image analyzing system and method thereof may further include a computer-assisted detection/diagnosis module configured to input at least one patient image to the image preprocessing module and the patch cropping module to generate a plurality of patient image patches and input the plurality of patient image patches into the full model to obtain a plurality of first prediction values corresponding to the respective plurality of patient image patches.

In the aforementioned medical image analyzing system and method thereof, the computer-assisted detection/diagnosis module further enables the threshold selection module to calculate at least one second prediction value corresponding to the at least one patient image based on the plurality of first prediction values respectively corresponding to the plurality of patient image patches, and plot a second curve based on the at least one second prediction value to determine a second threshold that is used for determining whether the at least one patient image is cancerous according to the second curve.

In the aforementioned medical image analyzing system and method thereof, the at least one second prediction value is a ratio between a number of patient image patches that are predicted as cancerous in the at least one patient image generated by applying the first threshold to the plurality of first prediction values respectively corresponding to each of the plurality of patient image patches and the total number of the plurality of patient image patches.

The aforementioned medical image analyzing system and method thereof further comprises a feature selection module configured to generate a feature importance ranking based on a plurality of features corresponding to the plurality of feature values in the full model, and enable the training module to train a reduced model using the feature value of at least one of the plurality of features of each of the plurality of image patches to obtain a plurality of first reduced prediction values corresponding to the respective plurality of image patches, and enable the threshold selection module to plot a first reduced curve based on the plurality of first reduced prediction values.

In the aforementioned medical image analyzing system and method thereof, the feature importance ranking is ranked according to the numbers of occurrences of the features, the gain values of the features, or any combination thereof.

In the aforementioned medical image analyzing system and method thereof, the feature selection module enables the training module to train the reduced model using the feature value of a feature starting from the top of the feature importance ranking.

In the aforementioned medical image analyzing system and method thereof, the computer-assisted detection/diagnosis module further inputs the plurality of patient image patches into the reduced model to obtain a plurality of first reduced prediction values respectively corresponding to the plurality of patient image patches, and enables the threshold selection module to calculate at least one second reduced prediction value corresponding to the at least one patient image based on the plurality of first reduced prediction values respectively corresponding to the plurality of patient image patches, and plot a second reduced curve based on the at least one second reduced prediction value.

In the aforementioned medical image analyzing system and method thereof, if the area under receiver operating characteristic curve (AUC) of the first reduced curve does not equate to or approximate the AUC of the first curve, or the AUC of the second reduced curve does not equate to or approximate the AUC of the second curve, the feature selection module enables the training module to train the reduced model using not only the feature value of the feature that is ranked first in the feature importance ranking, but also the feature value of a subsequent feature that is ranked next in the feature importance ranking iteratively until the AUCs of the first reduced curve and the second reduced curve equate to or approximate the AUCs of the first curve and the second curve, respectively.

Based on the foregoing, the medical image analyzing system and the method thereof according to the present disclosure can effectively assist radiologists in reducing the miss rate of clinical diagnosis of pancreatic cancer, and has a high sensitivity, in particular, for tumors smaller than 2 cm in size. Therefore, the situation that about 40% of tumors smaller than 2 cm evade detection may be effectively improved.

DETAILED DESCRIPTION OF THE EMBODIMENTS

The following describes the implementation of the present disclosure by embodiments, and those skilled in the art can easily understand other advantages and effects of the present disclosure based on the contents disclosed in this specification, or implement or apply the present disclosure based on other different specific embodiments.

Figure 1A:
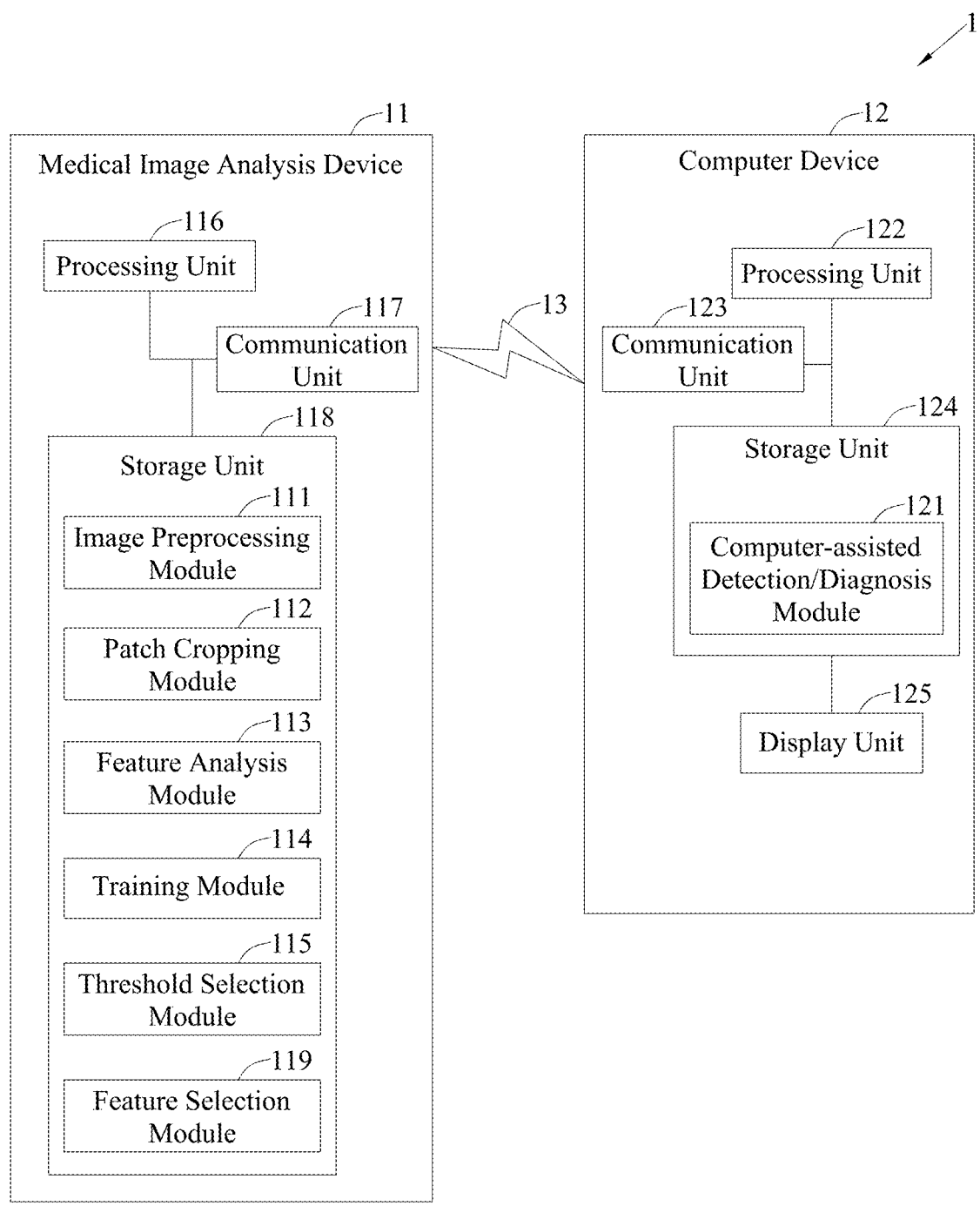
FIG. 1A is a schematic diagram illustrating a first embodiment of a medical image analyzing system according to the present disclosure.

FIG. 1A is a schematic diagram illustrating a first embodiment of a medical image analyzing system according to the present disclosure. The medical image analyzing system 1 may comprise a medical image analysis device 11 and a computer device 12 electrically connected to the medical image analysis device 11, wherein the medical image analysis device 11 and the computer device 12 communicate with each other through a wired or wireless network 13.

The medical image analysis device 11 comprises an image preprocessing module 111, a patch cropping module 112, a feature analysis module 113, a training module 114 and a threshold selection module 115, and further comprises a processing unit 116, a communication unit 117 and a storage unit 118, of which the communication unit 117 and the storage unit 118 are coupled to the processing unit 116. In addition, the medical image analysis device 11 may be, for example, a mobile phone, a tablet computer, a notebook computer, a desktop computer, a server or a cloud server, of which the present disclosure is not limited thereto. Moreover, the medical image analysis device 11 may further comprise a display unit, such as a screen or a monitor (not shown).

In an embodiment, the processing unit 116 may be a central processing unit (CPU), a microprocessor, a graphics processing unit (GPU), or an application-specific integrated circuit (ASIC). The communication unit 117 may be a component supporting signal transmission of various mobile communication systems (e.g., GSM, PHS, CDMA, WCDMA, LTE, WiMAX, 4G, 5G, etc.), Wi-Fi systems, Bluetooth systems or Ethernet. The storage unit 118 may be any type of a fixed or portable random access memory (RAM), read-only memory (ROM), flash memory, hard disk, soft disk, database, other similar components or a combination of the above, of which the present disclosure is not limited thereto.

In this embodiment, the image preprocessing module 111, the patch cropping module 112, the feature analysis module 113, the training module 114 and the threshold selection module 115 may be a program code segment, software or firmware stored in the storage unit 118, respectively, and may be executed by the processing unit 116, of which the present disclosure is not limited thereto. The image preprocessing module 111, the patch cropping module 112, the feature analysis module 113, the training module 114 and the threshold selection module 114 in the medical image analysis device 11 may also be implemented using other types of hardware or a hybrid of hardware and software.

The computer device 12 may comprise a computer-assisted detection/diagnosis module 121, and may also comprise a processing unit 122, a communication unit 123, a storage unit 124 and a display unit 125. In this embodiment, the processing unit 122, the communication unit 123 and the storage unit 124 may be components that are the same as or similar to the aforementioned processing unit 116, communication unit 117 and storage unit 118, respectively, and thus will not be further described. The computer-assisted detection/diagnosis module 121 may be a program code segment, software or firmware stored in the storage unit 124, and may be implemented using other types of hardware or a hybrid of hardware and software and executed by the processing unit 122. In addition, the computer device 12 may also be, for example, a mobile phone, a tablet computer, a notebook computer or a desktop computer, etc., and the display unit 125 may be a screen or a monitor, of which the present disclosure is not limited thereto.

Figure 1B:
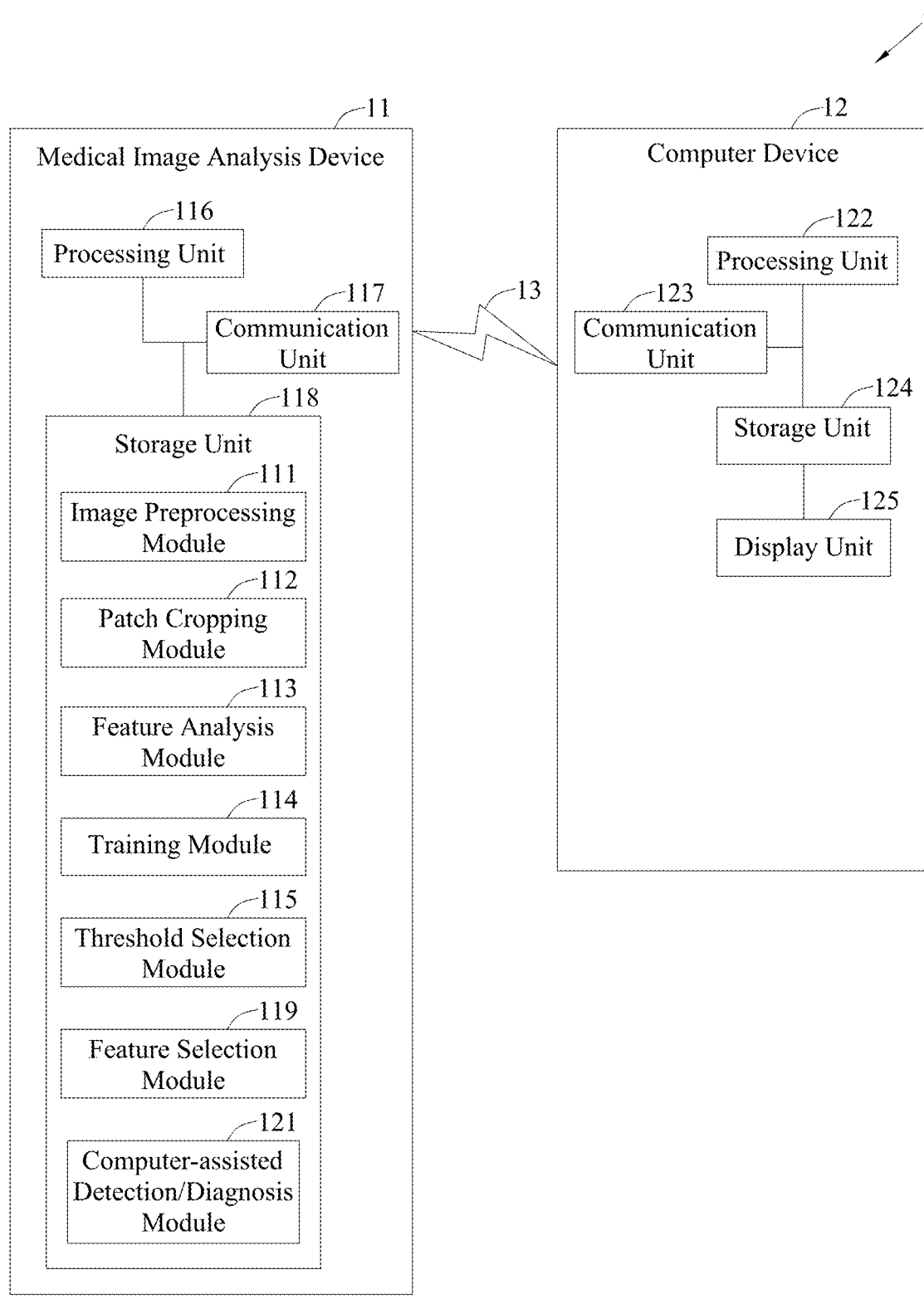
FIG. 1B is a schematic diagram illustrating a second embodiment of the medical image analyzing system according to the present disclosure.

Referring to FIG. 1B, which is a schematic diagram illustrating a second embodiment of the medical image analyzing system according to the present disclosure. The difference between the second embodiment and the aforementioned first embodiment is that the computer-assisted detection/diagnosis module 121 is provided in the medical image analysis device 11, instead of the computer device 12. Therefore, all computations can be performed on the medical image analysis device 11, while the computer device 12 is only a device that simply receives and displays outputs from the medical image analysis device 11, such that no high-end hardware is required for the computer device 12.

Figure 1C:
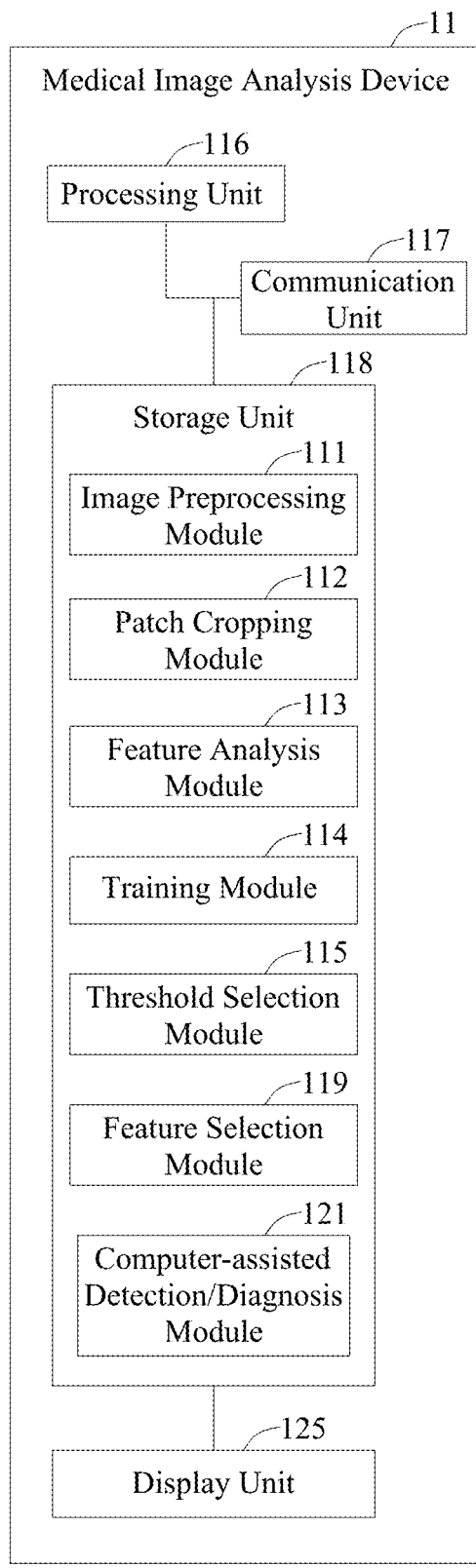
FIG. 1C is a schematic diagram illustrating a third embodiment of the medical image analyzing system according to the present disclosure.

Referring to FIG. 1C, which is a schematic diagram illustrating a third embodiment of the medical image analyzing system according to the present disclosure. The difference between the third embodiment and the aforementioned second embodiment is that the medical image analyzing system of the present disclosure may comprise only the medical image analysis device without the computer device. The medical image analysis device of the medical image analyzing system of the present disclosure not only may be the aforementioned mobile phone, tablet computer, notebook computer or desktop computer, server or cloud server, but also may be a computed tomography (CT) equipment or magnetic resonance imaging (MRI) equipment. In other words, the medical image analyzing system of the present disclosure may be installed in a CT equipment or a MRI equipment, of which the present disclosure is not limited thereto.

The detailed technical content of the aforementioned modules used in the medical image analyzing systems of FIG. 1A to FIG. 1C are described below.

Figure 2A:
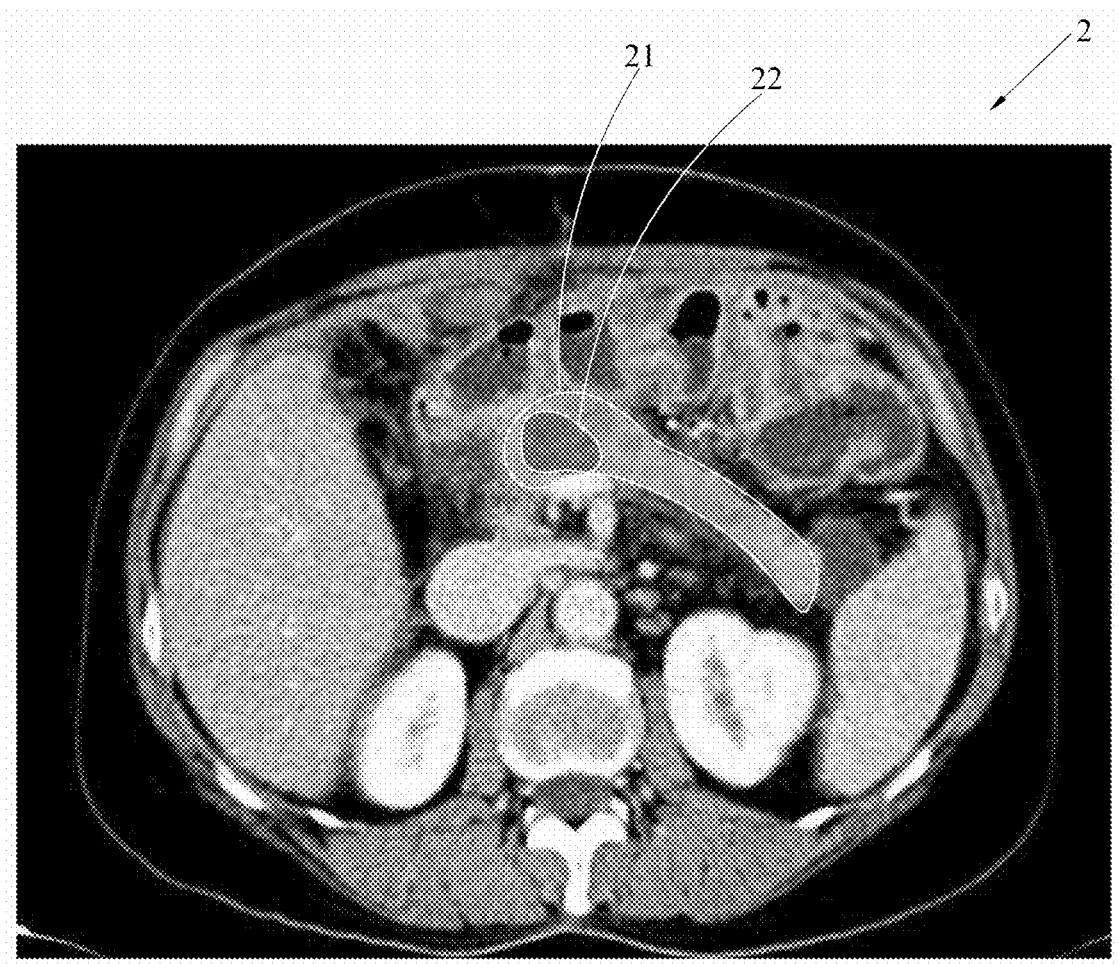
FIG. 2A is a schematic diagram illustrating a computed tomography image used as a training image by a medical image analyzing system according to the present disclosure.
Figure 2B:
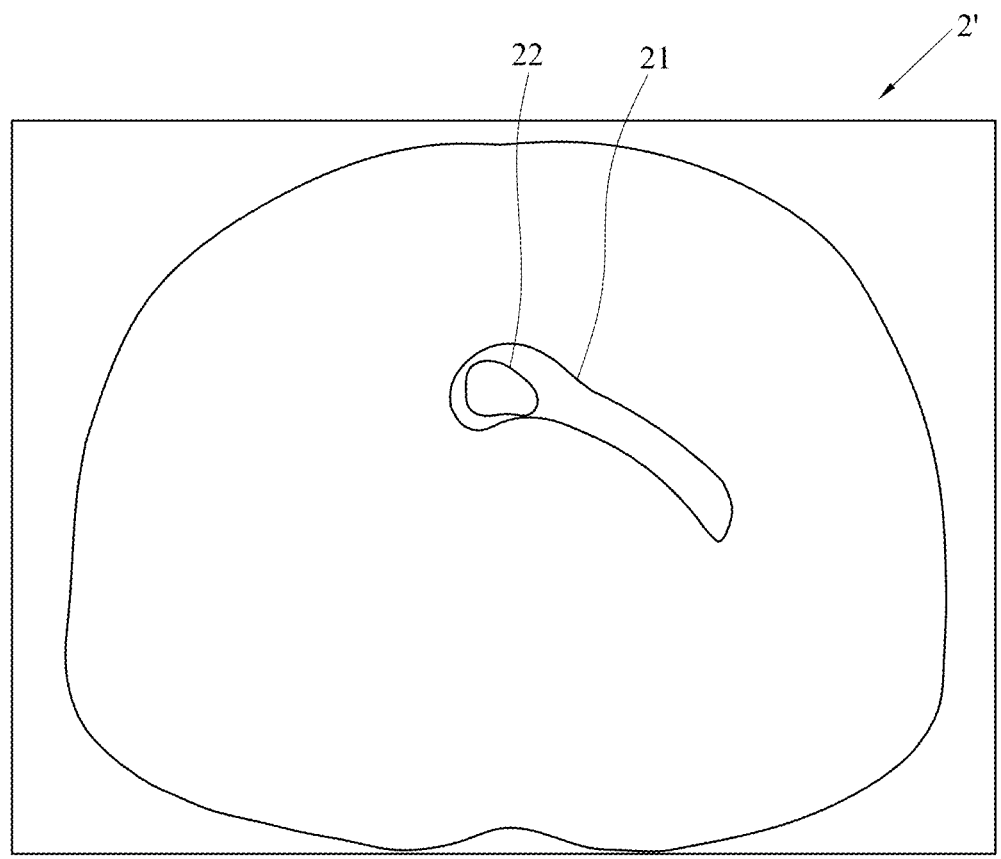
FIG. 2B to FIG. 2D are simplified schematic diagrams illustrating image preprocessing and generation of image patches of FIG. 2A.

FIG. 2A is a schematic diagram illustrating a computed tomography image denoted as an image 2 used in a medical image analyzing system according to the present disclosure. An organ 21 may be, for example, a pancreas. FIG. 2B is a simplified schematic diagram of FIG. 2A. The simplification made in FIG. 2B is only for the convenience of description and does not limit the present disclosure in any way. Referring to FIG. 2A in connection with FIG. 2B, the image preprocessing module 111 is configured to process at least one image 2 corresponding to an organ 21 to generate at least one processed image 2', of which the processed image 2' is marked with a segmentation label 22 corresponding to a cancerous area in the organ 21. The segmentation label 22 may be generally known as a region of interest (ROI). In this embodiment, the image 2 is pre-processed by the image preprocessing module 111. More specifically, the image 2 is a two-dimensional (2D) image or a three-dimensional (3D) image generated by CT or MRI. Taking a 2D CT image as an example, a patient typically has a plurality of 2D CT images. First, linear interpolation and nearest-neighbor interpolation are used respectively to resample the images 2 into an interval of 1×1×5 mm, such that the resolutions of all the images are the same. The linear interpolation can act on the entire image, and the nearest-neighbor interpolation can act on the ROI, with which the present disclosure is not limited thereto. In an embodiment, there are a plurality of the images 2, hence will also be a plurality of the processed images 2', where the present disclosure is not limited thereto.

Figure 2C:
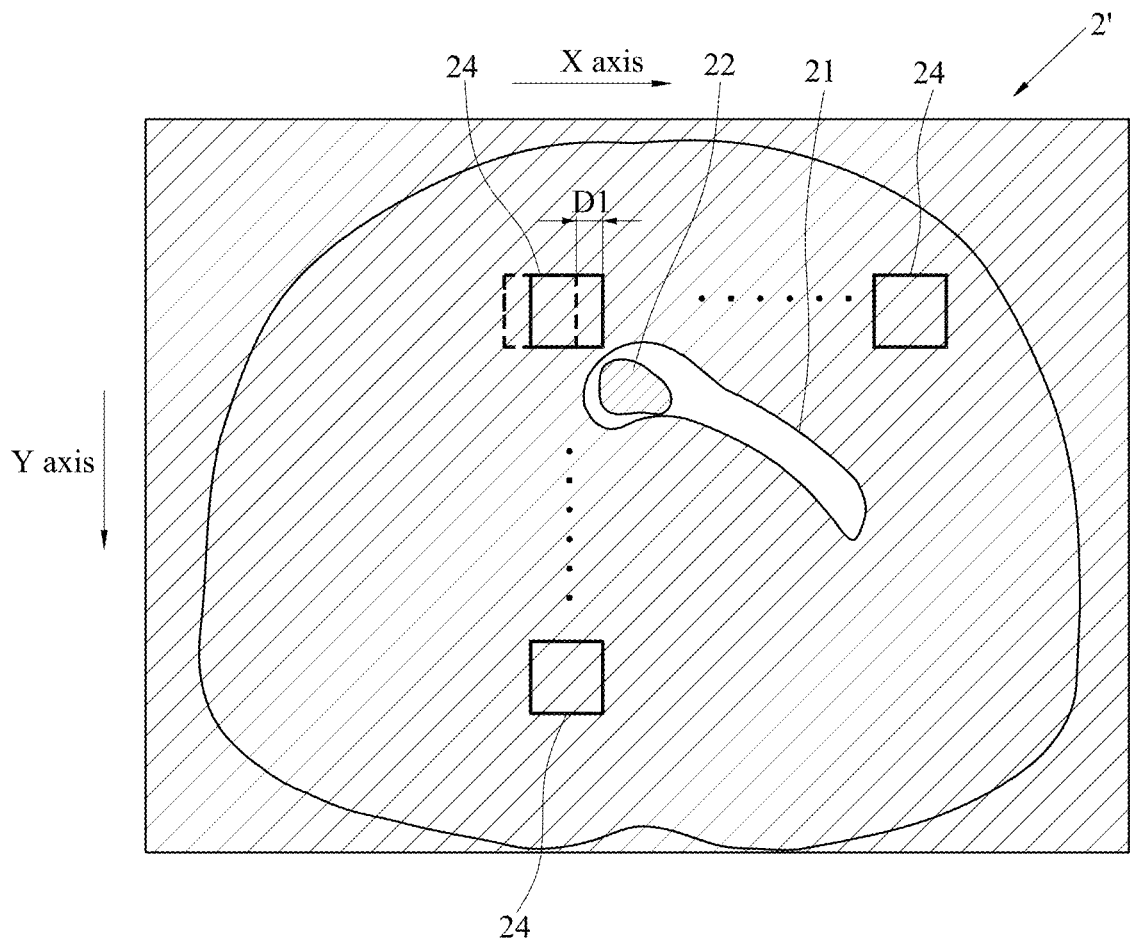
Figure 2D:
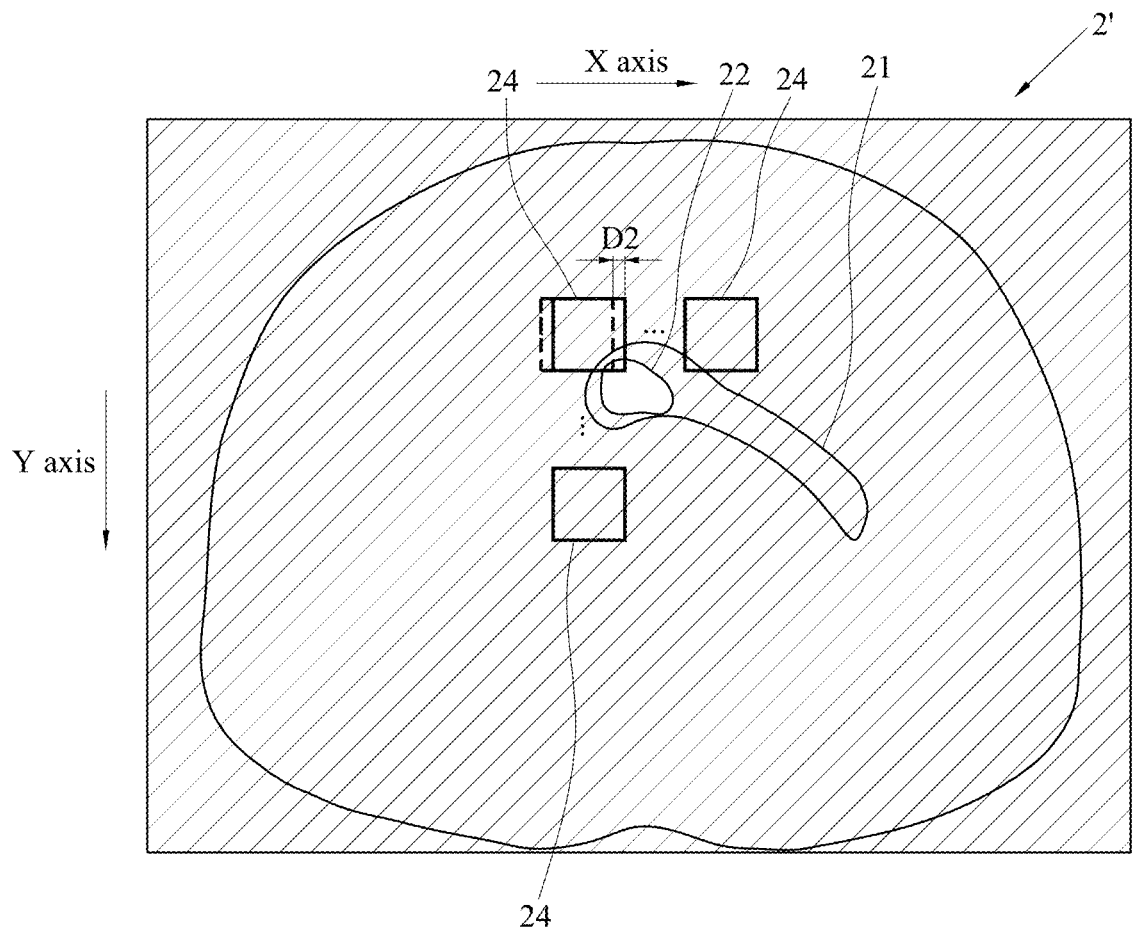
Figure 3:
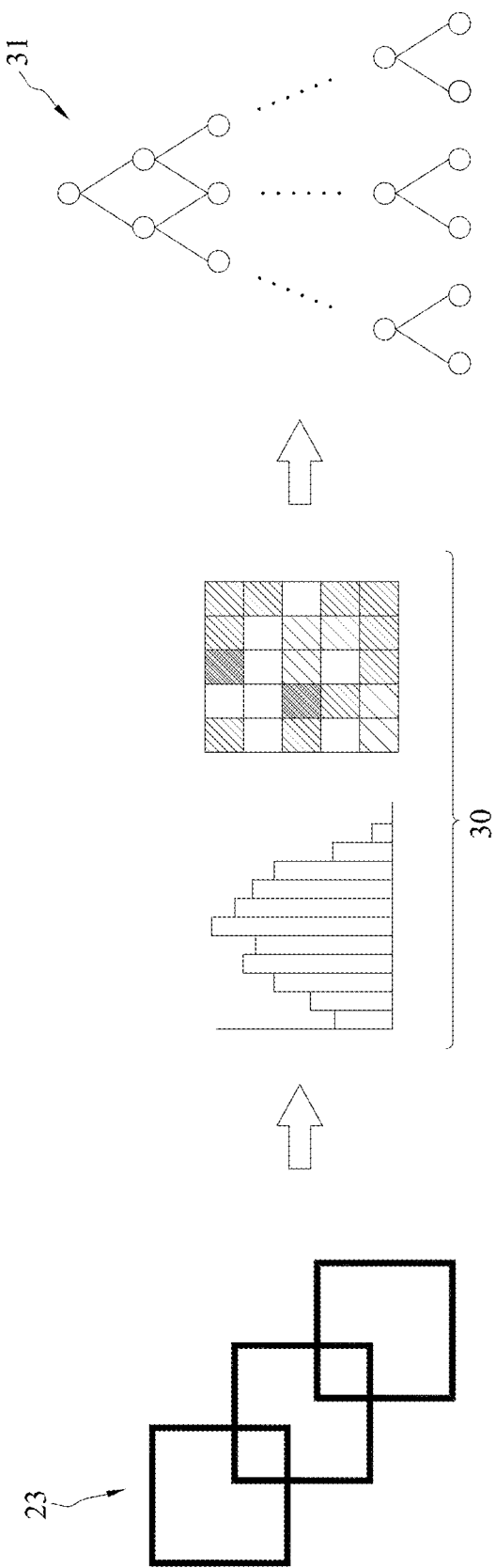
FIG. 3 is a schematic diagram illustrating the training of a full model in a medical image analyzing system according to the present disclosure.

Referring to FIG. 2C and FIG. 2D, the patch cropping module 112 is configured to acquire a plurality of image patches 23 (as shown in FIG. 3) from the processed image 2'. In this embodiment, the patch cropping module 112 acquires the plurality of image patches 23 from the processed image 2' using a square window 24 that moves along an x axis and a y axis of the processed image 2'. For example, the square window 24 may be 20×20 pixels in size, of which the present disclosure is not limited thereto.

In this embodiment, the patch cropping module 112 acquires image patches differently for areas inside the segmentation label 22 and outside the segmentation label 22 of the processed image 2'. As shown in FIG. 2C, the patch cropping module 112 will first mask the area of the segmentation label 22 as well as the area outside the organ 21 of the processed image 2' (masked areas are shown by diagonal lines), such that the square window 24 will not acquire images inside the segmentation label 22 or outside of the organ 21 (alternatively, the images acquired from inside the segmentation label 22 or outside of the organ 21 are discarded before the generation of image patches). Further, the square window 24 generates a plurality of image patches by acquiring the unmasked area of the processed image 2' at a stride of 5 pixels (e.g., a moving distance of D1). In a further embodiment, as shown in FIG. 2D, the patch cropping module 112 will mask all the processed image 2' except for the segmentation label 22 (masked areas are shown by diagonal lines), such that the square window 24 does not acquire image other than inside the segmentation label 22 (alternatively, images acquired from outside the segmentation label are discarded before the generation of image patches). Further, the square window 24 acquires the unmasked area of the processed image 2' at a stride of 1 pixel (e.g., a moving distance of D2). Whether in circumstance of FIG. 2C or FIG. 2D, the patch cropping module 112 may move the square window 24 from left to right and from top to bottom on the images to be acquired to generate a large amount of image patches 23, from which the present disclosure is not limited thereto.

After aforementioned acquisition by the patch cropping module 112, the generated image patches 23 may effectively include non-cancerous patches (acquired at a stride of 5 pixels from area inside the organ 21 in the processed image 2' except the area of the segmentation label 22) and cancerous patches (acquired at a stride of 1 pixel from the area of the segmentation label 22 in the processed image 2'). However, not all of the image patches 23 are subject to subsequent processing. The quantity of the image patches 23 can be appropriately adjusted to be between 10 and 200 (for example, the number of image patches 23 can be reduced to be within 200 by fixing a specific stride if the quantity of the image patches 23 exceeds 200, or the like). In addition, since the segmentation label 22 and the area other than the segmentation label 22 are acquired at different strides, the overlap density of each of the cancerous patches will be higher than that of the non-cancerous patches. In subsequent training, repetitive detections can take place to improve accuracy.

In an embodiment, only an image patch 23 containing a cancerous part of more than 50% of its total area can be labelled as a cancerous patch; otherwise, it is labelled as a non-cancerous patch. However, if the number of cancerous patches labelled based on the above method is less than 10, said labelling criteria can be altered. For example, the labelling criteria may be altered as: an image patch 23 containing a cancerous part of more than 5% of its total area is labelled as a cancerous patch; otherwise, it is labelled as a non-cancerous patch. However, the present disclosure is not limited to those described above. In an embodiment, the processed image 2' may also contain no cancerous part and is acquired at a stride of 5 pixels, so as to train the full model in a later process, of which the present disclosure is note limited thereto.

As shown in FIG. 3, after obtaining the plurality of image patches 23, the feature analysis module 113 can perform feature analysis on the plurality of image patches 23 to obtain a plurality of feature values for each of the image patches 23. In this embodiment, the feature analysis module 113 performs feature analysis using radiomics 30 (e.g. PyRadiomics version 2.2.0). The so-called radiomics is capable of extracting quantitative information related to density, shape or texture of an image, analyzing the radiomic features through machine learning algorithms, and building classification/regression models through example learning in order to present patterns/rules in the image that cannot be recognized by the naked eye. Radiomics 30 can analyze various types of features, and the features employed by this embodiment include: First Order features, Gray Level Co-occurrence Matrix (GLCM) features, Gray Level Dependence Matrix (GLDM) features, Gray Level Run Length Matrix (GLRLM) features, Gray Level Size Zone Matrix (GLSZM) features or Neighboring Gray Tone Difference Matrix (NGTDM) features. However, the features employed by the radiomics of the present disclosure are not limited to those above, and may exclude shape-based features, features that may be influenced by the volume of the analyzed object, including energy, total energy, and root mean squared included in the first order features, and the like.

In an embodiment, the radiomics of the present disclosure may choose 15 first order features, 22 GLCM features, 14 GLDM features, 16 GLRLM features, 16 GLSZM features and 5 NGTDM features, that is, a total of 88 features (as listed more specifically in Table 1 below) for feature analysis, and the interval or bin width of a histogram (shown in FIG. 3, for example) for calculating texture features is set to 25. As a result of feature analysis of each of the image patches 23, a plurality of feature values can be obtained for each of the image patches 23. For example, when 88 features are selected, feature values corresponding to the 88 features can be obtained for a single image patch 23.

TABLE 1

| | |
|---|---|
| First Order Features | 10 percentile, 90 percentile, entropy, interquartile range, kurtosis, maximum, mean, mean absolute deviation, median, minimum, range, robust mean absolute deviation, skewness, uniformity, variance |
| Gray Level Co-occurrence Matrix (GLCM) Features | autocorrelation, cluster prominence, cluster shade, cluster tendency, contrast, correlation, difference average, difference entropy, difference variance, ID, IDM, IDMN, IDN, IMC1, IMC2, inverse variance, joint average, joint energy, joint entropy, maximum probability, sum entropy, sum squares |
| Gray Level Dependence Matrix (GLDM) Features | dependence entropy, dependence non uniformity, dependence non uniformity normalized, dependence variance, gray level non uniformity, gray level variance, high gray level emphasis, large dependence emphasis, large dependence high gray level emphasis, large dependence low gray level emphasis, low gray level emphasis, small dependence emphasis, small dependence high gray level emphasis, small dependence low gray level emphasis. |
| Gray Level Run Length Matrix (GLRLM) Features | gray level non uniformity, gray level non uniformity normalized, gray level variance, high gray level run emphasis, long run emphasis, long run high gray level emphasis, long run low gray level emphasis, low gray level run emphasis, run entropy, run length non uniformity, run length non uniformity normalized, run percentage, run variance, short run emphasis, short run high gray level emphasis, short run low gray level emphasis |
| Gray Level Size Zone Matrix (GLSZM) Features | gray level non uniformity, gray level non uniformity normalized, gray level variance, high gray level zone emphasis, large area emphasis, large area high gray level emphasis, large area low gray level emphasis, low gray level zone emphasis, size zone non uniformity, size zone non uniformity normalized, small area emphasis, small area high gray level emphasis, small area low gray level emphasis, zone entropy, zone percentage, zone variance |
| Neighboring Gray Tone Difference Matrix (NGTDM) Features | busyness, coarseness, complexity, contrast, strength |

Once the respective plurality of feature values of each of the plurality of image patches 23 are obtained, the training module 114 may then train a full model using the plurality of feature values of each of the plurality of image patches 23 to obtain a plurality of first prediction values correspond to the respective image patches 23. In this embodiment, the training module 114 employs an extreme gradient boosting (XGboost) machine learning algorithm 31 (XGboost version 1.0.2) to train the full model (or so-called XGBoost model) to classify cancerous and non-cancerous patches.

As shown in FIG. 3, the so-called extreme gradient boosting (XGboost) machine learning algorithm 31 can sequentially build a plurality of decision trees in series in order to achieve classification. The plurality of decision trees are constructed by: building one decision tree and adding another decision tree thereafter, so that the latter decision tree reduces the classification errors of the previous decision tree. As a result, each decision tree can minimize the classification errors of the previous decision tree, and a full model combines the classifications predicted by all the decision trees. Moreover, the extreme gradient boosting (XGboost) machine learning algorithm may also quantify the importance (e.g. gain value) of each feature in the model efficiency.

In this embodiment, after the training module 114 has trained the full model, the full model can provide a corresponding first prediction value for each image patch 23, which is used for classification. For example, each image patch 23 can be classified as cancerous or non-cancerous using a first threshold. A method for determining the first threshold is described as follows.

Figure 4:
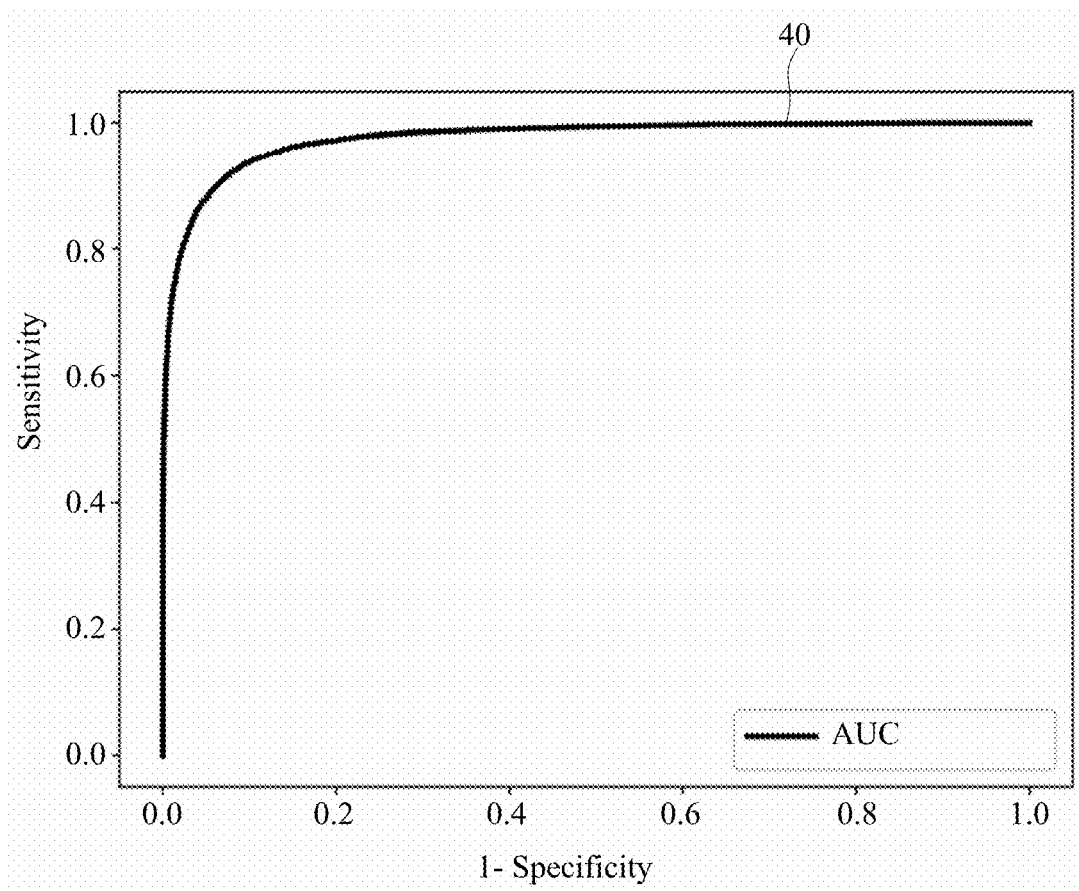
FIG. 4 is a schematic diagram illustrating a receiver operating characteristic curve plotted by a medical image analyzing system according to the present disclosure.

The threshold selection module 115 can plot a first curve based on the plurality of first prediction values and determine a first threshold for determining whether each of the plurality of image patches 23 is cancerous therefrom. More specifically, the plurality of image patches 23 respectively have a plurality of corresponding first prediction values. The plurality of first prediction values are compared against a specific threshold (for example, if a first prediction value is greater than the specific threshold, then the corresponding image patch is determined as cancerous), and then statistical indicators corresponding to the specific threshold, including sensitivity and specificity, etc., can be calculated, in which any value between 0 and 1 (e.g., 0.1, 0.2, 0.3, 0.4 . . . etc.) is a possible value for the specific threshold. In this way, a receiver operating characteristic curve (ROC) 40 as shown in FIG. 4 can be plotted according to the plurality of sensitivities and specificities calculated based on the possible values of the plurality of specific thresholds, and statistical indicators such as the area under receiver operating characteristic curve (AUC) and a plurality of Youden indexes can be obtained from the ROC curve 40, of which the Youden indexes (whose formula would be: Youden index=sensitivity−[1−specificity]) can be calculated from the sensitivity and specificity corresponding to each point on the ROC curve 40. In the present disclosure, the first threshold is determined as the threshold corresponding to the maximum value in the plurality of Youden indexes. When the first prediction value of an image patch is greater than the first threshold, the image patch may be classified as cancerous (positive). When the first prediction value of an image patch is less than or equal to the first threshold, the image patch may be classified as non-cancerous (negative).

In an embodiment, a true positive is defined as when both the full model of the present disclosure and the radiologist determine an image patch as cancerous; and a true negative is defined as when both the full model of the present disclosure and the radiologist determine the image patch as non-cancerous; a false positive is defined as when the full model of the present disclosure determines an image patch as cancerous but the radiologist determines the image patch as non-cancerous; and a false negative is defined as when the full model of the present disclosure determines an image patch as non-cancerous but the radiologist determines the image patch as cancerous. The aforementioned sensitivity and specificity are defined by the following formula: sensitivity=true positive/(true positive+false negative); specificity=true negative/(true negative+false positive).

The computer-assisted detection/diagnosis module 121 is configured to input at least one patient image to the image preprocessing module 111 and the patch cropping module 112 to generate a plurality of patient image patches corresponding to the at least one patient image and input the plurality of patient image patches to the full model to obtain a plurality of first prediction values corresponding to the respective plurality of patient image patches.

More specifically, the computer-assisted detection/diagnosis module 121 may be realized as a computer-assisted detection/diagnosis tool (CAD tool) software, and the computer-assisted detection/diagnosis module 121 may use the full model trained by the training module 114 of the medical image analysis device 11 to assist clinicians in patient diagnosis. For example, the clinician can first obtain a patient image of a patient to be analyzed, and input the patient image into the image preprocessing module 111 and the patch cropping module 112 of the medical image analysis device 11 through the computer-assisted detection/diagnosis module 121 of the computer device 12 to generate a plurality of patient image patches. The processing method of the patient image using the image preprocessing module 111 and the patch cropping module 112 is the same as that of the aforementioned image 2, and thus will not be described further herein. Next, the plurality of patient image patches of the patient is inputted into the full model to obtain a plurality of first prediction values corresponding to the respective plurality of patient image patches. Then, the computer-assisted detection/diagnosis module 121 enables the threshold selection module 115 to calculate at least one second prediction value corresponding to the at least one patient image according to the plurality of first prediction values corresponding to the respective plurality of patient image patches. In an embodiment, one patient corresponds to one second prediction value, while the patient still corresponds to one second prediction value even if said patient has more than one patient images. The second prediction value is calculated based on the plurality of first prediction values of the same patient, with which the present disclosure is not limited thereto. In this embodiment, after the plurality of first prediction values corresponding to the respective plurality of image patches are compared against the first threshold determined by the threshold selection module 115, the threshold selection module 115 classifies the plurality of patient image patches as cancerous (positive) or non-cancerous (negative). The second prediction value is generated based on count of the number of the patient image patches classified as cancerous in the at least one patient images. For example, the second prediction value may be a ratio between the number of patients image patches classified as cancerous in the at least one patient image and the total number of the plurality of patient image patches of the at least one patient images. In this embodiment, the computer-assisted detection/diagnosis module 121 may be configured to input a single patient image to obtain a single second prediction value which provides to clinicians information regarding whether the patient image is cancerous or not as determined by the computer-assisted detection/diagnosis module 121. The computer-assisted detection/diagnosis module 121 may also input a plurality of patient images (i.e., from different patients) to obtain a plurality of second prediction values for plotting a second curve in order to determine a second threshold subsequently. However, the present disclosure is not limited thereto. In addition, the aforementioned single patient image may be one or more 2D CT images taken for a single patient, such that the second prediction value can correspond to a single patient image. The single patient image can also be one or more 3D CT images taken for a single patient. The one or more 3D CT images may be processed by the image preprocessing module 111 to generate a plurality of 2D patient images, such that the second prediction value can also correspond to the plurality of patient images (which can also directly correspond to the patient). However, the present disclosure is not limited thereto.

Next, the computer-assisted detection/diagnosis module 121 enables the threshold selection module 115 to plot a second curve based on the plurality of second prediction values to determine a second threshold for determining whether each of the plurality of patient images is cancerous according to the second curve. The second curve is a receiver operating characteristic curve and the second threshold is the threshold corresponding to the maximum value of Youden indexes. The plotting of the second curve and the determination method of the second threshold are the same as those of the first curve and the first threshold, and thus will not be further described herein. After the second threshold is determined, the computer-assisted detection/diagnosis module 121 can compare the second prediction value corresponding to the patient image with the second threshold to determine whether the patient image is cancerous. For example, after a patient image is processed by the various modules and the full model, the second prediction value arrives at 0.7. If the second threshold is 0.5, the computer-assisted detection/diagnosis module 121 can give the result that the patient image is cancerous. If the second threshold is 0.8, the computer-assisted detection/diagnosis module 121 can give the result that the patient image is non-cancerous.

In an embodiment, the medical image analyzing system 1 of the present disclosure may further comprise a feature selection module 119 configured to generate a feature importance ranking based on the plurality of features corresponding to the plurality of feature values in the full model to re-train a reduced model and plot a first reduced curve. More specifically, the full model trained by the aforementioned feature analysis module 113 and the training module 114 can be obtained after analyzing all the features (e.g. 88 features). However, if problems such as computational speed, overfitting, reproducibility, versatility etc. are taken into consideration, some of the features can be eliminated to obtain a reduced model that is similar or equal to the full model in terms of performance. The purpose of the feature selection module 119 is to obtain this reduced model.

The feature selection module 119 first produces a feature importance ranking based on the plurality of features corresponding to the plurality of feature values in the full model. In this embodiment, the feature importance ranking is created by ranking features according to the numbers of occurrences of the features, the gain values of all the features in the full model, or a combination of the above. Said combination is referred to various arrangements between the gain values of the features and the number of occurrences of the features. For example, one such arrangement is an average gain value obtained from dividing the gain value of a feature by the number of occurrences of the feature, in which the present disclosure is not limited thereto. Using the gain value of a feature as an example, the gain value may represent the amount of contribution provided by the feature during model training. The higher the gain value, the higher the significance, and this gain value can be obtained upon training of the full model is completed. Table 2 below shows the ranking of the first 14 features in a full model and their gain values.

TABLE 2

| Feature | Gain Value |
|---|---|
| First order: median | 670.4 |
| NGTDM: busyness | 654.5 |
| GLCM: cluster shade | 425.5 |
| First order: 90 percentile | 405.2 |
| First order: skewness | 169.8 |
| GLDM: gray level non-uniformity | 161.1 |
| GLDM: large dependence low gray level emphasis | 123.2 |
| First order: interquartile range | 88.5 |
| GLDM: dependence non-uniformity | 80.0 |
| GLCM: correlation | 74.9 |
| GLRLM: run length non-uniformity normalized | 69.7 |
| First order: mean | 65.3 |
| GLCM: sum entropy | 62.8 |
| GLRLM: run entropy | 59.4 |

After the feature importance ranking is created by the feature selection module 119, the training module 114 can train a reduced model using the feature value(s) of at least one of the plurality of features of the plurality of image patches to obtain a plurality of first reduced prediction values corresponding to the respective plurality of image patches. The threshold selection module 115 will plot a first reduced curve (e.g. the ROC curve shown in FIG. 4) based on the plurality of first reduced prediction values. In an embodiment, the feature selection module 119 may first input a feature value of a feature that is ranked first in the feature importance ranking (e.g. "First order: median" shown in Table 2) into the training module 114, such that the training module 114 trains the reduced model using only the feature value of the feature in the first rank.

Once the reduced model is trained and the first reduced curve is plotted, the computer-assisted detection/diagnosis module 121 may further input a plurality of patient image patches into the reduced model to obtain a plurality of first reduced prediction values corresponding to the respective plurality of patient image patches. Then, the computer-assisted detection/diagnosis module 121 enables the threshold selection module 115 to calculate at least one second reduced prediction value corresponding to at least one patient image based on the plurality of first reduced prediction values corresponding to the respective plurality of patient image patches, and plot a second reduced curve. The only difference between the aforementioned first reduced prediction values, the second reduced prediction values, the first reduced curve and the second reduced curve and the aforementioned first prediction values, the second prediction values, the first curve and the second curve is whether they are generated from analyzing the features with the full model or the reduced model, and their similarities will not be further described herein.

The feature selection module 119 may compare the area under receiver operating characteristic curve (AUC) of the first reduced curve and the AUC of the first curve, and compare the AUC of the second reduced curve and the AUC of the second curve. If the AUC of the first reduced curve does not equate to or approximate (comparison basis can be rounded to the second decimal place) the AUC of the first curve, or the AUC of the second reduced curve does not equate to or approximate the AUC of the second curve, the feature value of a feature that is ranked as second in the feature importance ranking can be added for training the reduced model again. For example, both the "First order: median" and "NGTDM: busyness" in Table 2 are used in training a new reduced model, and a first reduced curve, a second reduced curve and their AUCs are generated again. At this stage, the AUCs of the newly generated first and second reduced curves are compared with the AUCs of the first and second curves to determine if they are equal or approximately equal (comparison basis can be rounded to the second decimal place), respectively. As long as one of them is not equal or approximately equal, then the feature value of a feature that is ranked as third in the feature importance ranking can be added to re-train the reduced model. For example, the "First order: median", "NGTDM: busyness" and "GLCM: cluster shade" in Table 2 are all used to train a new reduced model, and a first reduced curve, a second reduced curve and their AUCs are generated again. This training step is iterated until the AUCs of the first and second reduced curves equate to or approximate the AUCs of the first and second curves, respectively. Since the gain values of all the features in the full model may vary, it is possible that the effectiveness of the reduced model equates to or approximates the full model when only the feature values of a few of the foremost features are used for generating the reduced model. As a result, the number of features used is reduced, meaning computational speed may increase, problems of overfitting may be avoided, reproducibility and versatility may be raised, and interpretability and reliability can also be improved.

In an embodiment, the features ultimately selected for the reduced model may include: mean, 90 percentile and median in the first order features; busyness in the NGTDM feature; gray level non uniformity in the GLSZM feature; and dependence non uniformity in the GLDM feature. In the aspect of distinguishing cancerous patches from non-cancerous patches, the first three features are positively correlated with the intensity of the gray level image (for example, cancerous patches generally exhibit lower values in these three features), and the latter three features are positively correlated with heterogeneity (for example, cancerous patches generally exhibit higher values in these three features). As a result, cancerous patches can be effectively distinguished from non-cancerous patches. However, the present disclosure is not limited thereto, for example, the features ultimately selected by the reduced model can also be the first 14 features listed in Table 2.

Figure 5:
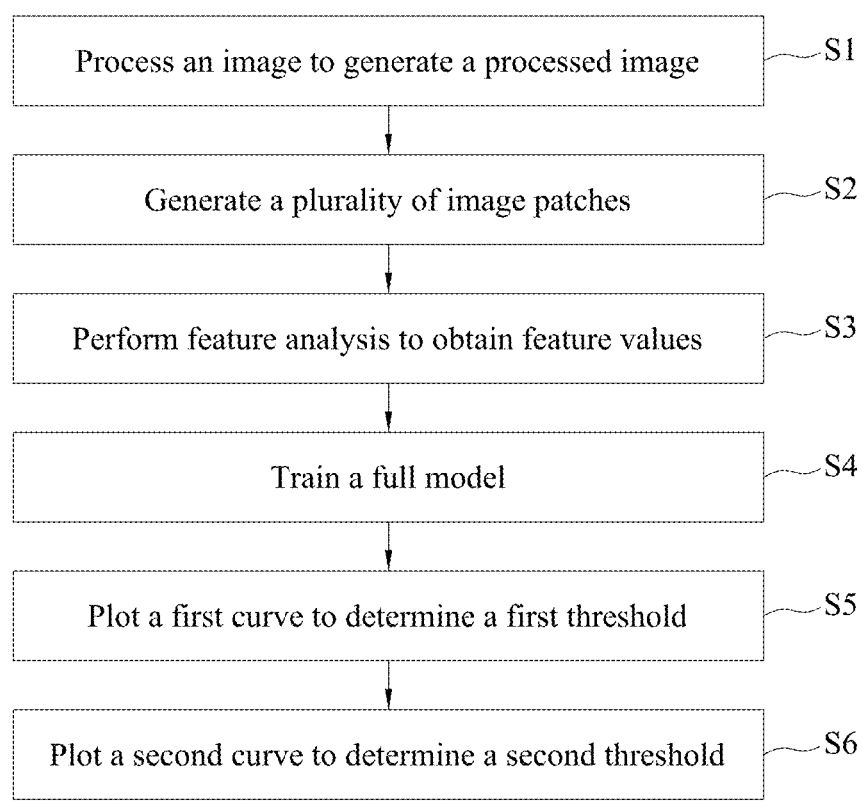
FIG. 5 is a flowchart illustrating an embodiment of a medical image analyzing method according to the present disclosure.

Referring to FIG. 5, a schematic flow chart of an embodiment of a medical image analyzing method according to the present disclosure is disclosed, and the medical image analyzing method according to the present disclosure may be used in the medical image analyzing system 1 having the medical image analysis device 11 as described above. The technical content of the medical image analyzing method of the present disclosure that are the same as those of the aforementioned medical image analyzing system will not be further described herein.

First, the medical image analyzing method according to the present disclosure may process an image to generate a processed image (step S1). That is, the medical image analyzing method according to the present disclosure enables the image preprocessing module 111 of the medical image analysis device 11 to process at least one image 2 corresponding to an organ 21 to generate at least one processed image 2', of which the processed image 2' is marked with a segmentation label 22 corresponding to a cancerous area of the organ 21.

Next, the medical image analyzing method according to the present disclosure may acquire a plurality of image patches (step S2). That is, the patch cropping module 112 of the medical image analysis device 11 is configured to acquire a plurality of image patches 23 from the processed image 2'.

Then, the medical image analyzing method according to the present disclosure performs feature analysis to obtain feature values (step S3). That is, the feature analysis module 113 of the medical image analysis device 11 is configured to perform feature analysis on the plurality of image patches 23 to obtain a plurality of feature values corresponding to the respective plurality of image patches, in which the feature analysis is performed using radiomics, where its technical content has already been described above and will not be further described herein.

Thereafter, the medical image analyzing method according to the present disclosure trains a full model (step S4). That is, the training module 114 of the medical image analysis device 11 is configured to train a full model using the plurality of feature values of the respective plurality of image patches to obtain a plurality of first prediction values respectively corresponding to the plurality of image patches, with which an extreme gradient boosting (XGboost) machine learning algorithm is used to train the full model, where its technical content has already been described above and will not be further described herein.

Next, the medical image analyzing method according to the present disclosure plots a first curve to determine a first threshold (step S5). That is, the threshold selection module 115 of the medical image analysis device 11 is configured to plot a first curve based on the plurality of first prediction values and determine a first threshold for determining whether each of the plurality of image patches 23 is cancerous according to the first curve.

Finally, after the full model is trained and the first threshold is determined, the medical image analyzing method according to the present disclosure may plot a second curve to determine a second threshold (step S6). That is, the computer-assisted detection/diagnosis module 121 of the computer device 12 electrically connected to the medical image analysis device 11 or the computer-assisted detection/diagnosis module 121 in the medical image analysis device 11 is configured to input at least one patient image to the image preprocessing module 111 and the patch cropping module 112 to generate a plurality of patient image patches, and the plurality of patient image patches are input into the full model to obtain a plurality of first prediction values respectively corresponding to the plurality of patient image patches. The computer-assisted detection/diagnosis module 121 further enables the threshold selection module 115 to calculate at least one second prediction value corresponding to the at least one patient image based on the plurality of first prediction values respectively corresponding to the plurality of patient image patches, and plot a second curve based on at least one second prediction value to determine a second threshold that determines whether the at least one patient image is cancerous, of which the second curve is a receiver operating characteristic curve and the second threshold is a threshold corresponding to the maximum value of the Youden indexes. In this embodiment, the plurality of second prediction values are the ratio between the number of patient image patches that are classified as cancerous in the at least one patient image by applying the first threshold to the plurality of first prediction values respectively corresponding to each of the plurality of patient image patches and the total number of the plurality of the patient image patches.

Figure 6:
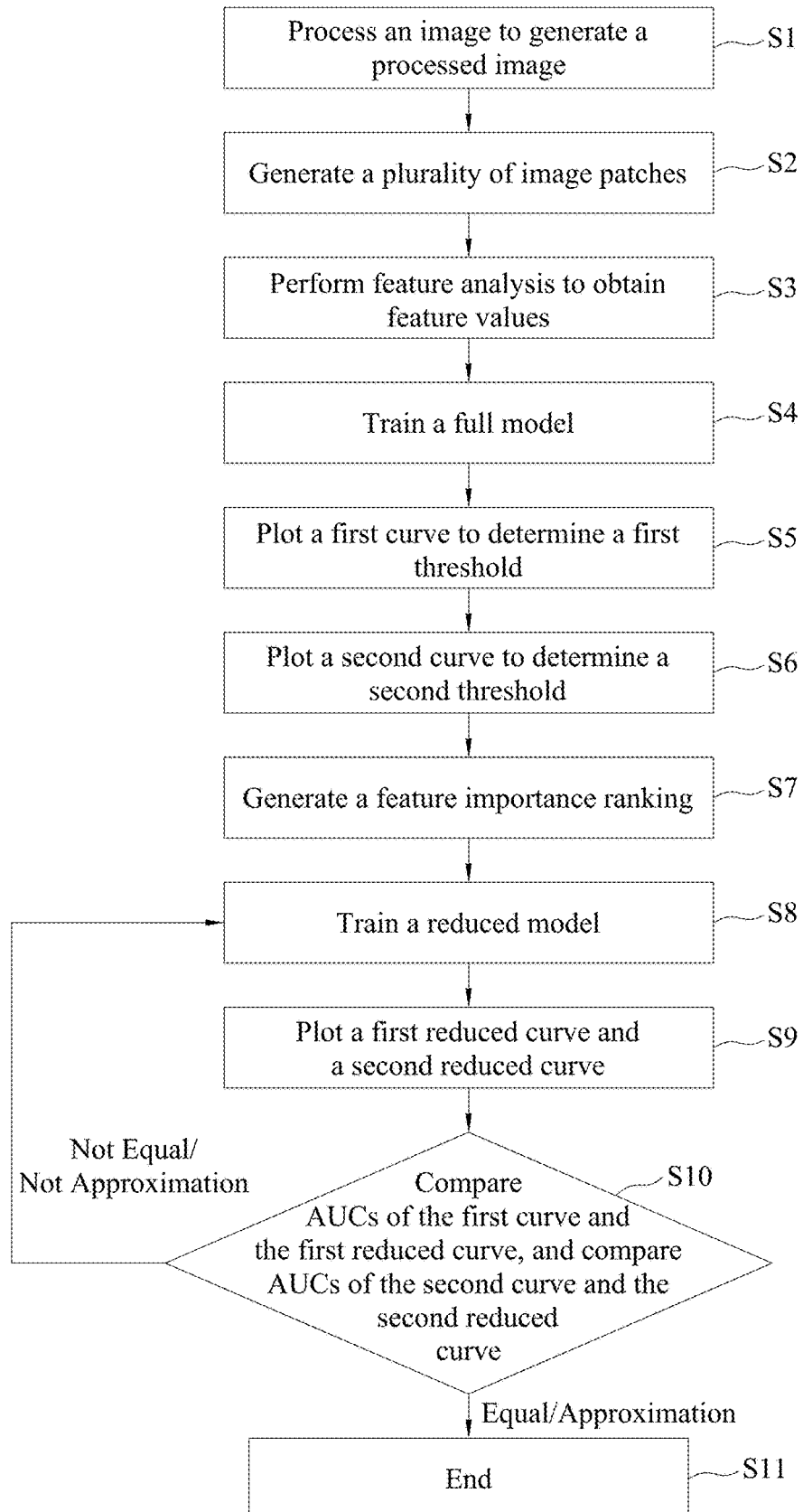
FIG. 6 is a flowchart illustrating an alternative embodiment of the medical image analyzing method according to the present disclosure.

Referring to FIG. 6, a schematic flow chart of another embodiment of the medical image analyzing method according to the present disclosure is disclosed. In this embodiment, the steps S1 to S6 in FIG. 6 are the same as steps S1 to S6 in FIG. 5. The following only describes steps S7 to S11, and the same technical content will not be further described herein.

In step S7, a feature importance ranking is created based on the plurality of features corresponding to the plurality of feature values in the full model, of which the feature importance ranking is ranked according to the numbers of occurrences of the features, the gain values of the features, or a combination of the above, where the present disclosure is not limited thereto. Next, proceed to step S8.

In step S8, a reduced model is trained using the feature value of at least one of the plurality of the features of the respective plurality of image patches. More specifically, the reduced model is trained by using the feature value of feature starting from the top-ranked feature in the feature importance ranking (e.g. the "First order: median" in Table 2). Then, proceed to step S9.

In step S9, a plurality of first reduced prediction values respectively corresponding to the plurality of image patches are obtained based on the trained reduced model, and a first reduced curve is plotted based on the plurality of first reduced prediction values. Similarly, a plurality of first reduced prediction values respectively corresponding to the plurality of patient image patches are obtained based on the trained reduced model to calculate at least one second reduced prediction value corresponding to the at least one patient image, and a second reduced curve is plotted. The first reduced curve or the second reduced curve can be, for example, the receiver operating characteristic (ROC) curve shown in FIG. 4. Then, proceed to step S10.

In step S9, the area under receiver operating characteristic curve (AUC) of the first reduced curve is compared with the AUC of the first curve, and the AUC of the second reduced curve is compared with the AUC of the second curve. If the AUC of the first reduced curve does not equate to or approximate (comparison basis can be rounded to the second decimal place) the AUC of the first curve, or the AUC of the second reduced curve does not equate to or approximate (comparison basis can be rounded to the second decimal place) the AUC of the second curve, then return to step S8 to re-train the reduced model. In addition to the feature value of the top-ranked feature in the feature importance ranking, the feature value of a feature that is ranked as second in the feature importance ranking can be added in re-training of the reduced model. For example, both the "First order: median" and "NGTDM: busyness" in Table 2 are used in training a new reduced model, and a first reduced curve, a second reduced curve and their AUCs are generated again (step S9). At this stage, the AUC of the newly generated first reduced curve is compared with the AUC of the first curve to determine if they are equal or approximately equal, or the AUC of the newly generated second reduced curve is compared with the AUC of the second curve to determine if they are equal or approximately equal (step S10). As long as one of them is not equal or approximately equal, then return to step S8, where the feature value of a feature that is ranked as third in the feature importance ranking can be used in re-training of the reduced model. For example, the "First order: median", "NGTDM: busyness" and "GLCM: cluster shade" in Table 2 are used to train a new reduced model, and a first reduced curve, a second reduced curve and their AUCs are generated again (step S9). Steps S8 to S10 are iterated until the AUCs of the first and second reduced curves equate to or approximate the AUCs of the first and second curves, respectively (step S11).

The performance of the medical image analyzing system and method thereof of the present disclosure is demonstrated below: first, 34,164 image patches labelled as cancerous and 100,955 image patches labeled as non-cancerous were taken from 349 patients with pancreatic cancer and 383 patients without cancers and used as model training materials. A full model and a reduced model were trained using the aforementioned number of image patches. The area under receiver operating characteristic curve (AUC) with the full model reached 0.965 with sensitivity, specificity and accuracy being 0.931, 0.953 and 0.943, respectively. The area under receiver operating characteristic curve (AUC) with the reduced model reached 0.972 with sensitivity, specificity and accuracy being 0.954, 0.940 and 0.947, respectively.

Furthermore, 8,224 image patches labelled as cancerous and 26,989 image patches labeled as non-cancerous were taken from 87 patients with pancreatic cancer and 96 patients without cancers and used as validation model materials. The aforementioned image patches were input into the reduced model. The area under receiver operating characteristic curve (AUC) obtained was 0.969 with sensitivity, specificity and accuracy being 0.966, 0.938 and 0.951, respectively. Its sensitivity is higher than the sensitivity of 0.952 of radiologists.

Moreover, 6,020 image patches labelled as cancerous and 29,053 image patches labeled as non-cancerous were taken from 100 patients with pancreatic cancer and 100 patients without cancers and used as model validation materials. The aforementioned image patches were input into the reduced model. The area under receiver operating characteristic curve (AUC) obtained was 0.937 with sensitivity, specificity and accuracy being 0.910, 0.900 and 0.905, respectively. Its sensitivity is higher than the sensitivity of 0.895 for radiologists.

Looking at the statistics of the tumor sizes of the aforementioned cancer patients and the sensitivities between the medical image analyzing system and method thereof according to the present disclosure and radiologists, it was concluded that when detecting tumor sizes less than 2 cm, the sensitivity of the reduced model according to the present disclosure was 0.909, whereas the sensitivity of radiologists was only 0.900. When detecting tumor sizes larger than 2 cm, the sensitivity of the reduced model according to the present disclosure was 0.947, whereas the sensitivity of radiologists was only 0.930.

Based on the foregoing, the medical image analyzing system and the method thereof according to the present disclosure can effectively assist radiologists in reducing the miss rate of clinical diagnosis for pancreatic cancer, and has a high sensitivity, in particular, for tumors smaller than 2 cm in size. Therefore, the situation where about 40% of tumors smaller than 2 cm being undetectable in general clinical context is effectively improved. Moreover, it should be noted that the medical image analyzing system and the method thereof according to the present disclosure is not limited to application of diagnosis of pancreatic cancer, but are also applicable to the diagnosis of other symptoms.

The above embodiments are only set forth to illustrate the principles of the present disclosure, and should not be interpreted as to limit the present disclosure in any way. The above embodiments can be modified or altered by one of ordinary skill in the art without departing from the spirit and scope of the present disclosure. Any modification and alternatives achieved by utilizing the teaching of the present disclosures are considered to be included within the claims described below. The claimed protection scope for the present disclosure are defined in the appended claims attached below.

What is claimed is:

1. A medical image analyzing system, comprising:
   an image preprocessing module, executed by a processor, configured to process at least one image corresponding to an organ to generate at least one processed image, wherein the processed image comprises a segmentation label corresponding to a cancerous part of the organ;
   a patch cropping module, executed by the processor, configured to acquire a plurality of image patches from the processed image;
   a feature analysis module, executed by the processor, configured to perform feature analysis on the plurality of image patches to obtain a plurality of feature values corresponding to each of the plurality of image patches;
   a training module, executed by the processor, configured to train a full model using the plurality of feature values of each of the plurality of image patches to obtain a plurality of first prediction values corresponding to the respective plurality of image patches;

a threshold selection module, executed by the processor, configured to plot a first curve based on the plurality of first prediction values and determine a first threshold that is used for determining whether each of the plurality of image patches is cancerous according to the first curve; and a computer-assisted detection/diagnosis module, executed by the processor, configured to input at least one patient image to the image preprocessing module and the patch cropping module to generate a plurality of patient image patches and input the plurality of patient image patches into the full model to obtain a plurality of first prediction values corresponding to the respective plurality of patient image patches, wherein the computer-assisted detection/diagnosis module further enables the threshold selection module to calculate at least one second prediction value corresponding to the at least one patient image based on the plurality of first prediction values respectively corresponding to the plurality of patient image patches, and plot a second curve based on the at least one second prediction value to determine a second threshold that is used for determining whether the at least one patient image is cancerous according to the second curve.

2. The medical image analyzing system of claim 1, wherein the patch cropping module acquires the plurality of image patches with a square window that moves along an x axis and a y axis of the processed image.

3. The medical image analyzing system of claim 2, wherein the patch cropping module masks the segmentation label of the processed image and masks the processed image except for the organ, and then acquires an unmasked area of the processed image with the square window moving at a stride of 5 pixels to generate the plurality of image patches.

4. The medical image analyzing system of claim 2, wherein the patch cropping module masks the processed image except for the segmentation label, and then acquires an unmasked area of the processed image with the square window moving at a stride of 1 pixel to generate the plurality of image patches.

5. The medical image analyzing system of claim 1, wherein the feature analysis module performs feature analysis using radiomics.

6. The medical image analyzing system of claim 5, wherein features employed by the radiomics include: First Order features, Gray Level Co-occurrence Matrix (GLCM) features, Gray Level Dependence Matrix (GLDM) features, Gray Level Run Length Matrix (GLRLM) features, Gray Level Size Zone Matrix (GLSZM) features or Neighboring Gray Tone Difference Matrix (NGTDM) features.

7. The medical image analyzing system of claim 1, wherein the training module trains the full model using an extreme gradient boosting (XGboost) machine learning algorithm.

8. The medical image analyzing system of claim 1, wherein the at least one second prediction value is a ratio between a number of patient image patches that are predicted as cancerous in the at least one patient image by applying the first threshold to the plurality of first prediction values respectively corresponding to each of the plurality of patient image patches and a total number of the plurality of patient image patches.

9. The medical image analyzing system of claim 1, further comprising a feature selection module, executed by the processor, configured to generate a feature importance ranking based on a plurality of features corresponding to the plurality of feature values in the full model, and enable the training module to train a reduced model using the feature value of at least one of the plurality of features of each of the plurality of image patches to obtain a plurality of first reduced prediction values corresponding to the respective plurality of image patches, and enable the threshold selection module to plot a first reduced curve based on the plurality of first reduced prediction values.

10. The medical image analyzing system of claim 9, wherein the feature importance ranking is ranked according to numbers of occurrences of the features, gain values of the features, or any combination thereof.

11. The medical image analyzing system of claim 9, wherein the feature selection module enables the training module to train the reduced model using the feature value of a feature starting from a top of the feature importance ranking.

12. The medical image analyzing system of claim 9, wherein the computer-assisted detection/diagnosis module further inputs the plurality of patient image patches into the reduced model to obtain a plurality of first reduced prediction values respectively corresponding to the plurality of patient image patches, and enables the threshold selection module to calculate at least one second reduced prediction value corresponding to the at least one patient image based on the plurality of first reduced prediction values respectively corresponding to the plurality of patient image patches, and plot a second reduced curve based on the at least one second reduced prediction value.

13. The medical image analyzing system of claim 12, wherein if an area under receiver operating characteristic curve (AUC) of the first reduced curve does not equate to or approximate an AUC of the first curve, or an AUC of the second reduced curve does not equate to or approximate an AUC of the second curve, the feature selection module enables the training module to train the reduced model using a feature value of the feature that is ranked first in the feature importance ranking and a feature value of a subsequent feature that is ranked next in the feature importance ranking iteratively until the AUCs of the first reduced curve and the second reduced curve equate to or approximate the AUCs of the first curve and the second curve, respectively.

14. A medical image analyzing method, comprising:
processing at least one image corresponding to an organ to generate at least one processed image, wherein the processed image comprises a segmentation label corresponding to a cancerous part of the organ;
acquiring a plurality of image patches from the processed image;
performing feature analysis on the plurality of image patches to obtain a plurality of feature values corresponding to each of the plurality of image patches;
training a full model using the plurality of feature values of each of the plurality of image patches to obtain a plurality of first prediction values corresponding to the respective plurality of image patches;
plotting a first curve based on the plurality of first prediction values and determining a first threshold that is used for determining whether each of the plurality of image patches is cancerous according to the first curve;
inputting at least one patient image to generate a plurality of patient image patches;
inputting the plurality of patient image patches into the full model to obtain a plurality of first prediction values corresponding to the respective plurality of patient image patches;
calculating at least one second prediction value respectively corresponding to the at least one patient image based on the plurality of first prediction values respectively corresponding to the plurality of patient image patches; and plotting a second curve based on the at least one second prediction value to determine a second threshold that is used for determining whether the at least one patient image is cancerous according to the second curve.

15. The medical image analyzing method of claim 14, wherein the plurality of image patches are acquired using a square window that moves along an x axis and a y axis of the processed image.

16. The medical image analyzing method of claim 15, further comprising masking the segmentation label of the processed image and masking the processed image except for the organ, and then acquiring an unmasked area of the processed image with the square window moving at a stride of 5 pixels to generate the plurality of image patches.

17. The medical image analyzing method of claim 15, further comprising masking the processed image except for the segmentation label, and then acquiring an unmasked area of the processed image with the square window moving at a stride of 1 pixel to generate the plurality of image patches.

18. The medical image analyzing method of claim 14, wherein feature analysis is performed using radiomics.

19. The medical image analyzing method of claim 18, wherein features employed by the radiomics include: First Order features, Gray Level Co-occurrence Matrix (GLCM) features, Gray Level Dependence Matrix (GLDM) features, Gray Level Run Length Matrix (GLRLM) features, Gray Level Size Zone Matrix (GLSZM) features or Neighboring Gray Tone Difference Matrix (NGTDM) features.

20. The medical image analyzing method of claim 14, wherein the full model is trained using an extreme gradient boosting (XGboost) machine learning algorithm.

21. The medical image analyzing method of claim 14, wherein the at least one second prediction value is a ratio between a number of patient image patches that are predicted as cancerous in the at least one patient image by applying the first threshold to the plurality of first prediction values respectively corresponding to the plurality of patient image patches and a total number of the plurality of patient image patches.

22. The medical image analyzing method of claim 14, further comprising generating a feature importance ranking based on a plurality of features corresponding to the plurality of feature values in the full model, and training a reduced model using the feature value of at least one of the plurality of features of each of the plurality of image patches to obtain a plurality of first reduced prediction values corresponding to the respective plurality of image patches, and plotting a first reduced curve based on the plurality of first reduced prediction values.

23. The medical image analyzing method of claim 22, wherein the feature importance ranking is ranked according to numbers of occurrences of the features, gain values of the features, or any combination thereof.

24. The medical image analyzing method of claim 22, wherein the reduced model is trained using a feature value of a feature starting from a top of the feature importance ranking.

25. The medical image analyzing method of claim 22, further comprising inputting the plurality of patient image patches into the reduced model to obtain a plurality of first reduced prediction values respectively corresponding to the plurality of patient image patches, and calculating at least one second reduced prediction value corresponding to the at least one patient image based on the plurality of first reduced prediction values respectively corresponding to the plurality of patient image patches, and plotting a second reduced curve based on the at least one second reduced prediction value.

26. The medical image analyzing method of claim 25, wherein if an area under receiver operating characteristic curve (AUC) of the first reduced curve does not equate to or approximate an AUC of the first curve, or an AUC of the second reduced curve does not equate to or approximate an AUC of the second curve, the reduced model is trained using a feature value of the feature that is ranked first in the feature importance ranking and a feature value of a subsequent feature that is ranked next in the feature importance ranking iteratively until the AUCs of the first reduced curve and the second reduced curve equate to or approximate the AUCs of the first curve and the second curve, respectively.

* * * * *